United States Patent [19]

Audhya et al.

[11] Patent Number: 5,036,050
[45] Date of Patent: Jul. 30, 1991

[54] COMPOSITIONS CONTAINING THYMOPENTIN FOR TOPICAL TREATMENT OF SKIN DISORDERS

[75] Inventors: Tapan Audhya, Bridgewater; Krishnamurthy Venkatasubramanian, South Somerville; Gideon Goldstein, Short Hills, all of N.J.

[73] Assignee: Immunobiology Research Institute, Inc., Annandale, N.J.

[21] Appl. No.: 452,757

[22] Filed: Dec. 19, 1989

Related U.S. Application Data

[63] Continuation-in-part of Ser. No. 296,137, Jan. 12, 1989, abandoned.

[51] Int. Cl.$^5$ .................. A61K 37/00; A61K 9/06
[52] U.S. Cl. ..................................... 514/17; 514/179; 530/330
[58] Field of Search ................. 424/401; 514/17, 179; 530/330

[56] References Cited

U.S. PATENT DOCUMENTS

| | | |
|---|---|---|
| 4,190,646 | 2/1980 | Goldstein et al. |
| 4,261,886 | 4/1981 | Goldstein et al. |
| 4,361,673 | 11/1982 | McGregor |
| 4,420,424 | 12/1983 | Geiger et al. |
| 4,428,938 | 1/1984 | Kisfaludy et al. |
| 4,505,853 | 3/1985 | Goldstein et al. |
| 4,547,489 | 10/1985 | Goldstein et al. |
| 4,614,517 | 9/1986 | Ruoslahti et al. |
| 4,629,723 | 12/1986 | Goldstein et al. |
| 4,742,048 | 5/1988 | Bouchaudon et al. |
| 4,749,690 | 6/1988 | Goldstein |
| 4,753,958 | 6/1988 | Weinstein .......................... 514/410 |

FOREIGN PATENT DOCUMENTS

| | | |
|---|---|---|
| 0235904 | 9/1987 | European Pat. Off. |
| 3633651 | 4/1988 | Fed. Rep. of Germany |
| 1404583 | 9/1975 | United Kingdom |

OTHER PUBLICATIONS

Liden, Surv. Immunol. Res., 4: Suppl. 1, pp. 24–29 (1985).
F. Pipino et al., Arzneim.-Forsch/Drug Res., 38:116–119 (1988).
G. Goldstein, Nature (London), 247:11–14 (1974).
R. S Basch et al., Proc. Natl. Acad. Sci. USA., 71:1474–1478 (1974).
M. P. Scheid et al., J. Exp. Med., 147:1727–1743 (1978), [Scheid I].
M. P. Scheid et al., Science, 190:1211–1213 (1975), [Scheid II].
G. E. Ranges et al., J. Exp. Med., 156:1057–1064 (1982).
K. Venkatasubramania et al., Proc. Nat. Acad. Sci. USA., 83:3171–3174 (1986).
M. G. Malaise et al., in "Immunoregulatory UCLA Symposium on Molecular and Cellular Biology", eds. G. Goldstein et al. (Liss, New York) (1986), [Malaise I].
G. H. Sunshine et al., J. Immunol., 120:1594–1599 (1978).
Kisfaludy et al., Hoppe-Seyler's Z. Physiol. Chem., B. D. 364, S. 933–940 (1983), [Kisfaludy I].
G. A. Heavner et al., Peptides, 7:1015 (1986).
T. Abiko et al., Chem. Pharm. Bull., 27(9):2233–2237 (1979), [Abiko I].
T, Abiko et al., Chem. Pharm. Bull., 28(8):2057–2511 (1980), [Abiko II].
T. Abiko et al., CHem. Pharm. Bull., 29(8):2322–2329 (1981), [Abiko III].
T. Abiko, Chem. Pharm. Bull., 29(11):3320–3325 (1981), [Abiko IV].
T. Abiko et al., J. A-pl. Biochem., 7:408–422 (1985), [Abiko V].
K. Kisfaludy et al., Ann. Immunol. Hung., 25:189–193 (1985). [Kisfaludy II].
E. Rentz, Arch. Geschwulstforsch, 54:113–118 (1984).
G. I. Chipens et al., Bioorganicheskaya Khimiya, 11(4):437–446, (1985).
Kessler et al., Liebigs. Ann. Chem., (1986), pp. 869–931 and German Application No. DE3401545 (1985).
E. Ivan et al., Arch. Toxical., Suppl. 8, pp. 495–498 (1985).
Chu et al., Journal of Investigative Dermatology, 81:194–197 (1983).
Audhya et al., Int. J. Peptide Protein Res., 22:568–572 (1983).
Malaise et al., The Lancet, 832–836 (1985).
Audhya et al., Biochem., 20:6195–6200 (1980).
Sundal et al., Immune Regulation by Characterized Peptides, 121–136 (Liss, New York) (1987).
A. Castells et al., Surv. Immunol. Res., 4:63–69, Suppl. 1 (1985).
J. DeMaubeuge et al., Surv. Immunol. Res., 4:30–36, Suppl. 1 (1985).
N. Friedmann, Surv. Immunol. Res., 4:139–154, Suppl. 1 (1985).
N. Clumeck et al., Int. J. Clin. Pharm. Res., IV(6):4-59–463 (1984).
W. Barcellini et al., Clin. Exp. Immunol., 67:537–543 (1987).

*Primary Examiner*—Howard E. Schain
*Assistant Examiner*—Choon Koh
*Attorney, Agent, or Firm*—Howson and Howson

[57] ABSTRACT

A composition for use in the topical treatment of skin disorders such as dermatitis or poison ivy, which comprises an effective amount of thymopentin and a suitable carrier is provided. A method for treating skin disorders and a method for making a topical composition are disclosed.

26 Claims, No Drawings ns characterized by an immunosuppressed state of
COMPOSITIONS CONTAINING THYMOPENTIN FOR TOPICAL TREATMENT OF SKIN DISORDERS This application is a continuation-in-part of U.S. patent application Ser. No. 296,137, filed Jan. 12, 1989, abandoned.

The present invention relates generally to the use of thymopentin in a formulation suitable for local topical treatment of a variety of skin disorders.

BACKGROUND OF THE INVENTION

The pentapeptide thymopentin is the active site of the naturally-occurring polypeptide thymopoietin. Both thymopoietin and thymopentin induce biological changes in two human T cell lines, MOLT-4 and CEM, thereby indicating their roles in stimulating helper and suppressor activities of T cells. The naturally-occurring polypeptide thymopoietin has been detected in basal cells of skin, although its function is uncertain [See, e.g., A. C. Chu et al, *J. Invest. Dermatol.*, 81:194 (1983)].

U.S. Pat. No. 4,190,646 discloses thymopentin as well as peptide compositions in which various groups are substituted onto the amino and/or carboxyl termini of this pentapeptide. See also, for example, G. Goldstein, *Nature* (London) 247: 11–14 (1974); R. S. Basch and G. Goldstein, *Proc. Natl. Acad. Sci. U.S.A.*, 71:1474–1478 (1974); M. P. Scheid et al., *J. Exp. Med.*, 147:1727–1743 (1978); M. P. Scheid et al., *Science*, 190:1211–1213 (1975); G. E. Ranges et al., *J. Exp. Med.*, 156:1057–1064 (1982); T. Audhya et al., *Biochem.* 20:6195–6200 (1981); K. Venkatasubramanian et al., *Proc. Natl. Acad. Sci. U.S.A.*, 83:3171–3174 (1986); M. G. Malaise et al., in "Immunoregulatory UCLA Symposium on Molecular and Cellular Biology", eds. G. Goldstein et al., (Liss, New York) (1986); G. G. Sunshine et al., *J. Immunol.*, 120:1594–1599 (1978) and E. Rentz et al., *Arch. Geschwulstforsch*, 54(2):113–118 (1948). See also U.S. Pat. Nos. 4,261,886; 4,361,673; 4,420,424; and 4,629,723. Reference is made to the above-described patents, applications and articles for a discussion of other background material and the biological processes involved in the present invention.

Thymopentin has been developed for pharmaceutical administration as a parenteral drug, and has proved valuable in treating systemically certain chronic infections characterized by an immunosuppressed state of the host. Conditions for which thymopentin has been employed therapeutically include lepromatous leprosy and severe recurrent herpes virus infections. This pentapeptide has also been employed in the treatment of certain allergies. Thymopentin has additionally been studied for the systemic treatment of atopic dermatitis.

Thymopentin has proved to be an outstandingly safe therapeutic agent for systemic parenteral administration in both a wide range of animal studies and extensive clinical trials for these and other conditions. [See, e.g., E. Sundal et al., "Therapy with thymopentin: A clinical overview", in *Immune Regulation by Characterized Peptides*, eds: G. Goldstein et al., Alan R. Liss, Inc. N.Y., pp 121–136 (1987); A. Castells et al., *Surv. Immunol. Res.*, 4:63–69, Suppl. 1 (1985); J. Demaubeuge et al, *Surv. Immunol. Res.*, 4:30–36, Suppl. 1 (1985); co-owned, copending U.S. patent application Ser. No. 822,704; N. Friedmann, *Surv. Immunol. Res.*, 4:139–154 Suppl. 1 (1985)].

Thymopentin has also been employed in experimental therapy with patients having acquired immunodeficiency syndrome, or AIDS, a disease predominantly caused by transmission of the retrovirus, HIV-1, and with a category of patients demonstrating symptoms of AIDS related complex, or ARC. [See, e.g., N. Clumeck et al., *Int. J. Clin. Pharm. Res.*, 4:459–463 (1984); W. Barcellini et al., *Clin. Exp. Immunol.*, 67:537–543 (1987)]

There has been no suggestion to date that thymopoietin or thymopentin are useful as other than systemically acting pharmaceutical agents for parenteral or intravenous administration.

SUMMARY OF INVENTION

As one aspect, the present invention provides a composition for use in the topical treatment of skin disorders or diseases. This composition contains an effective amount of thymopentin or an analog thereof and a suitable pharmaceutically acceptable carrier, such as a cream, ointment, gel or a lotion. The composition of the invention is useful in topically treating a number of skin disorders, including but not limited to, eczema, psoriasis, herpes simplex lesions, poison ivy, atopic dermatitis, chronic dermatitis, contact dermatitis and irritant dermatitis.

As yet another aspect, the invention provides a method for reducing the irritation of a skin disorder comprising administering directly onto the surface of a skin disorder on a mammal in need of such treatment, a topical formulation containing an effective amount of thymopentin or an analog thereof in a suitable pharmaceutical carrier.

Still another aspect of the present invention is a method for the preparation of a topical formulation of thymopentin or an analog thereof. Such a method may include the steps of micronizing thymopentin to a highly micronized state of approximately 2–5 microns for admixture into an emulsion of petroleum jelly or mineral oil, glycerin and fatty acid and alcohols. Careful mixing of the micronized thymopentin into the emulsion is required so that thymopentin or one of its analogs is distributed evenly throughout the emulsion.

Other aspects and advantages of the present invention are described more fully in the following detailed description of preferred embodiments thereof.

DETAILED DESCRIPTION OF THE INVENTION

The invention provides a composition for topical use on skin disorders which contains thymopentin or an analog thereof as the active ingredient. Although thymopentin has previously been described as a safe therapeutic agent for parenteral administration for systemic treatment of a variety of immune disorders, it has been unexpectedly discovered that thymopentin is effective in topically treating a variety of skin disorders when it is included as the active agent in specific pharmaceutical ointments and creams. No suggestion has been previously made that thymopentin would have efficacy as a topically delivered, locally active therapeutic agent.

The thymopentin for use in such compositions may be produced synthetically as described in U.S. Pat. No. 4,190,646, or by any other appropriate method. The various analogs of thymopentin described in the above-recited patents and references, and in copending U. S. patent applications Ser. No. 07/196,138; Ser. No.

07/268,692 and published PCT application PCT/US89/01967 and Ser. No. 07/252,505 and published PCT application PCT/US89/04000 which are incorporated by reference herein, may also prove suitable for inclusion into topical formulations. Throughout the remainder of this application for simplicity, the term "thymopentin" will mean the pentapeptide thymopentin and the analogs thereof described in the references identified above.

The compositions of the present invention may be made to suit particular treatment requirements of identified skin disorders, but generally will contain thymopentin in a concentration of about 0.01 to 10% of the total composition.

Suitable pharmaceutical carriers for the topical composition of the present invention may include several conventional ingredients of creams, lotions, gels or ointments. Such conventional ingredients are included in skin creams or oils for topical administration for treating a variety of diseases of the skin. Such compositions may be used as drug delivery systems to transmit pharmaceutical agents through the skin or to facilitate the absorption of a medicament into the skin or onto a rash or other skin eruption. See e.g. U.S. Pat. No. 3,981,996; U.S. Pat. No. 4,731,241; U.S. Pat. No. 4,164,563; U.S. Pat. No. 3,924,004; U.S. Pat. No. 3,888,995; U.S. Pat. No. 3,592,930; U.S. Pat. No. 4,753,958.

The composition of the present invention preferably contains thymopentin emulsified in an oil in water base, e.g., mineral oil. The composition may also contain thymopentin enclosed in the center of a micelle. The composition also contains at least one long chain alkyl or alkenyl compound of less than 18 carbon atoms having a lipophilic character and containing a hydrophobic end. Examples of such compounds are white petrolatum (petroleum jelly), stearic acid, microcrystalline waxes and acetylated lanolin having a viscosity of 200 ssu or greater at 30° C.

An essential component of the composition is an agent capable of penetrating the waxy surface of the skin, e.g., a detergent. Exemplary useful detergents for this compositions are: sodium lauryl sulfate (also called sodium dodecylsulfate) or polyoxyethylene 40 stearate. The absence of a detergent agent has been found to render the composition inactive. For example, no activity was detected in mixtures of thymopentin with just petroleum jelly and water, or in an oil base suspension or with beeswax and an alcohol.

Other ingredients may be present in the compositions of this invention, such as are conventionally present in oil-in-water emulsion pharmaceutical formulations. For example, the composition of the invention may optionally contain a moisture protecting agent, such as glycerin. This composition may also contain a fatty acid alcohol, e.g., stearyl alcohol, palmityl alcohol, maleic alcohol or cetyl alcohol. As with skin creams, in general, the present composition contains an aqueous medium, e.g. generally purified water.

Additionally free fatty acids having a maximum of 16 to 18 carbons in length may also be added to the composition. Such free fatty acids include stearate and palmitate, among others.

A pH stabilizer may be employed to buffer the composition, preferably to maintain a pH at about 7 or slightly higher, and increase the therapeutic longevity thereof. Exemplary pH stabilizers include glycine, although other known stabilizers may also be useful in this composition.

Other optional enhancers, e.g. inert ingredients which promote delivery of the thymopentin to the skin may be included, for example, M-pyrol, citrate, maleic acid, ethylenediaminetetraacetic acid, free amino acids and Carbopol.

Additionally, it is desirable to include a small amount of preservative in the composition of the present invention to enable storage of the compositions in good condition. Preservatives such as methyl and propyl paraben may be employed, as well as other known preservatives.

Among compositions which prove to be effective carriers for thymopentin topical compositions is the Unibase ® formula [Warner-Lambert Co.] containing purified water, cetyl alcohol, glycerin, stearyl alcohol, white petrolatum, sodium lauryl sulfate, granular sodium citrate and propylparaben. Other commercially available carrier ingredients of interest include Microthene, FN-510 or FA520 [Syntex] which make the composition nongreasy.

One presently preferred composition according to the invention contains the following components: about 0.1 to 10% thymopentin; about 30% of two fatty acid alcohols; about 3 to 4% glycerin; about 2 to 5% detergent; about 20% water; about 30 to 35% petroleum jelly; about 0 to 2% of a free fatty acid; an optional pH stabilizer; and one or more optional enhancers. Such a preferred composition is described in Example 1B below, employing the Unibase carrier.

Another more preferred composition according to this invention contains the following components: about 0.1 to about 10% thymopentin; about 2–7% of a fatty acid alcohol; about 1 to 3% glycerin; about 5 to 15% mineral oil; about 5 to 7 % detergent; about 0–3% of a free fatty acid; about 50–70% purified water; about 0 to 10% pH stabilizer, and about 0 to 0.3% preservative. One or more optional enhancers may also be added to this composition. Such a preferred composition is described in Example 1A below, as well as in Example 1C below.

It has presently been determined to be desirable in preparing such pharmaceutical compositions to micronize the thymopentin into a size range of 2 to 5 microns. This size enables the thymopentin to be distributed evenly in a oil in water base emulsion. Even distribution of the thymopentin is highly desirable for therapeutic activity.

It is critical that the formulation be prepared in a manner that slowly moisturizes the thymopentin and evenly disperses the cream to allow the thymopentin to penetrate the skin. A suitable temperature range should be employed in mixing the formulation ingredients. A temperature range of about 35°–75° C. is desirable for the mixing of the formulations of the present invention. For example, a temperature range of 30°–50° C. may be employed in mixing the ingredients of the formulation of Example 1C below. A temperature range of between about 70°–75° C. may be employed for the formulation of Examples 1A and 1B.

An additional critical element of the topical formulation is that, unlike many skin compositions which have a pH about 5, the thymopentin formula must have a pH of about 7 or higher.

The compositions of the invention may be employed to topically treat a variety of skin disorders to locally reduce itch, inflammation, or spread of a rash. Among the conditions which respond to treatment with topical application of thymopentin are various types of dermatitis, poison ivy, Herpes Simplex type 1 lesions. Other skin disorders which may be treated by the compositions of the invention are sunburn and other minor burns, eczema and psoriasis.

The dosage of a thymopentin topical formulation is desirably from about 0.01 to about 10% thymopentin. Applications of the compositions may range from one to three applications daily for the duration of the eruption on the skin. The appropriate dosage and application regimen will be determined by the attending physician considering various factors, including the type of skin disorder to be treated, extent and severity of outbreak, possible co-treatment with a systemically-acting medicament and other clinical factors.

The following examples describe the use of a topical formulation containing thymopentin according to the invention and illustrate several skin disorders which are successfully treated by the formulation of the invention. The efficacy of formulations containing thymopentin were studied using a neuromuscular assay on guinea pigs.

EXAMPLE 1

Compositions for Topical Administration of Thymopentin

Formulation A: A preferred formulation for topical administration of thymopentin is prepared as follows. In this description, percents are by weight unless otherwise specified. Thymopentin powder, prepared as described in U. S. Pat. No. 4,190,646, incorporated herein by reference, is micronized to 2 to 5 microns in the presence of dry air. 10 g of the micronized powder is moisturized in a desiccator under a humid atmosphere for 18–20 hours.

0.18% methylparaben (N.F.) is dissolved in 2.36% glycerine (U.S.P.) and added, with mixing, to 62.95% purified water (U.S.P.) with a 5% excess to compensate for loss due to evaporation. This mixture (Phase A) is heated and the temperature maintained to between 70°–75° C.

6.30% light mineral oil (USP) is heated to the same temperature range. The following ingredients are added to the mineral oil, with mixing, until all solids have melted: 2.80% glyceryl monostearate (NF), 1.80% polyoxyl 40 stearate (NF), 0.90 % myristyl myristate (CTFA), 2.80% stearyl alcohol (NF) and 0.09% propylparaben (NF). This mixture is referred to as Phase B.

While maintaining that temperature, Phase A is added to Phase B with continuous agitation until the mixture is homogenized. Mixing is continued while the resulting cream is allowed to cool to room temperature. Finally, a mixture of 10.00% thymopentin, prepared as described above, in 9.83% purified water is dissolved with mixing into the cooled cream.

Formulation B: A composition using a standard pharmaceutical carrier may also be employed in preparing a composition according to this invention. The thymopentin is micronized as described in Formulation A. To this moisturized powder, 90 g of Unibase ® [Warner-Lambert] is added and mixed thoroughly, resulting in a cream mixture containing 10% thymopentin.

Formulation C: Another composition is prepared according to the present invention as follows. All percentages are by weight. 15% light mineral oil (USP, Witco) is heated to between 30° to 50° C. To this heated base are added 3% glyceryl monostearate (Kodak), 3% polyoxyethylene 40 stearate (NF, ICI Chemicals), 7% cetosteryl alcohol (USP, Henkel) and 0.10 % propyl paraben (NF, Sutton Labs). These components are mixed until all solids have melted, the resulting melted composition comprising Phase B.

To prepare Phase A, 50.7% purified water (USP) with a 5% excess to compensate for loss due to evaporation is mixed with 10% glycine (USP, NF, Sigma) and 1% glycerine (USP, NF, Grace Organic Chemicals Div.) until dissolved. This mixture is heated to between 70° to 75° C., and 0.2 % methyl paraben (NF, Sutton Lab Inc.) is mixed therein until dissolved.

While maintaining the temperature, Phase A is slowly transferred to Phase B with continuous agitation until homogenized. The mixing is continued while the resulting cream is allowed to slowly cool to room temperature. To the cooled cream is added 10% thymopentin, made as described above, with continuous agitation.

The resulting cream is left overnight and mixed until homogenized. It may be stored at room temperature until needed. This is the presently most preferred formulation of thymopentin cream according to the present invention. Formulation B was actually used in the following Examples 2-6.

EXAMPLE 2

Neuromuscular Assay

To determine the effect of different formulations and dosages of compositions according to the invention, varying amounts of topical TP5 compositions prepared as described in Example 1B, were applied to the skin of guinea pigs.

A $1\frac{1}{2}'' \times 1\frac{1}{2}''$ square section was shaved on each animal's back 24 hours before the application of the thymopentin composition. Four concentrations of thymopentin cream were used (10%, 5%, 2.5% and 1.25%) using Unibase ® as a diluent. A total of 100 mg of cream containing either 10 mg, 5 mg, 2.5 mg or 1.25 mg thymopentin was rubbed with a spatula on the shaved skin of each animal. Control animals were treated similarly with the Unibase ® carrier only.

Eighteen hours later the neuromuscular transmission of each group of five animals for each concentration was assessed by electromyography as described in Lancet, 12:256–259 (1975). Significant neuromuscular change was observed in the guinea pigs treated with 10% and 5% thymopentin compared to the control animals, indicating systemic absorption of thymopentin.

EXAMPLE 3

Treatment of Herpes Virus Type 1 Skin Lesions

An adult subject had recurring outbreaks of Herpes Simplex Virus Type 1 lesions which created a prodrome, a palpable swelling or induration, a day prior to the actual eruption of the lesion on the surface of the skin. The subject detected the swelling and applied the composition described in Example 1 (e.g. about 100 mg of a 10% formula of thymopentin) directly on the swelling two times daily. This administration continued for from one to three days. The swelling was reduced and the lesion never appeared on the skin.

The same patient repeated this procedure several times upon the occurrences of palpable Herpes Simplex swelling, and the same results were documented.

EXAMPLE 4

Treatment of Poison Ivy

A subject patient had contracted poison ivy which had erupted into a red, itchy rash. The composition of Example 1 was applied to the rash twice daily. Within three days the itchy irritation of the rash was considerably reduced. Within a week of following this procedure, the itchiness was further subjectively reduced and the poison ivy did not proceed to the stage of blister formation. This outbreak of poison ivy was thus controlled and healed within a shorter time than required by the normal course of poison ivy. Additionally, the application of this topical composition containing thymopentin appeared to cut short the course of the poison ivy infection.

EXAMPLE 5

Treatment of Eczematic Dermatitis

One patient had an outbreak of eczematic dermatitis on the skin of his forearm. This subject applied the composition of Example 1 on the rash twice a day for two days. By the end of the second day, the itchiness of the rash was reduced and the rash itself also reduced in size and redness.

EXAMPLE 6

Treatment of Contact Dermatitis

One subject had a patch of contact dermatitis on his hand for approximately twelve years due to prior contact with 2-chloromethyl-4-nitrophenyl-4-dichlorodate. The appearance of this rash was reddened, scaling and indurated on the palm of the hand. The subject used the composition of Example 1 on the rash once a day for two to three days. This treatment subjectively alleviated the itchy irritation of the rash.

The subject then applied the composition of Example 1 on the rash twice a day for a week. Both the itch and the rash were both subjectively reduced in color and irritation within the week. The scaling was reduced and induration was reduced. The subject continued the application of the cream twice a day for three weeks. The rash had substantially disappeared from the hand.

The subject discontinued use of the cream and observed no change in the improved rash for about one week after application of the composition was discontinued. At that point, the rash began to return. The subject began to reuse the cream once a day for five days and again noticed an improvement in the scaling and the itchiness of the dermatitis.

The examples above are provided for illustration only and are not considered to limit the scope of the claims. For example, other suitable carrier formulations for thymopentin topical administration may be employed and are obvious to one of skill in the art considering the present disclosure. Similarly, other skin disorders than those described in the examples may be treated with the topical compositions containing thymopentin. Such modifications are encompassed by the scope of the following claims.

We claim:

1. A therapeutic composition for use in the treatment of a skin disorder comprising an effective amount of thymopentin or an analog thereof in a pharmaceutically acceptable carrier suitable for topical administration directly onto the surface of the skin.

2. The composition according to claim 1 wherein said amount is between about 0.1 to about 10% by weight thymopentin.

3. The composition according to claim 1 wherein said carrier is selected from the group consisting of a cream, a gel, an ointment and a lotion.

4. The composition according to claim 1 wherein said carrier is an oil-in-water emulsion.

5. The composition according to claim 1 further comprising at least one long chain alkyl or alkenyl compound of less than 18 carbon atoms having a lipophilic character and containing a hydrophobic end.

6. The composition according to claim 5 wherein said compound comprises a fatty acid or fatty alcohol selected from the group consisting of stearyl alcohol, cetyl alcohol, oleyl alcohol, maleic alcohol, or palmityl alcohol.

7. The composition of claim 1 further comprising a moisture protecting agent.

8. The composition of claim 7 wherein said moisture protecting agent is glycerin.

9. The composition according to claim 1 further comprising an agent capable of penetrating the waxy surface of the skin.

10. The composition according to claim 9 wherein said agent is a detergent.

11. The composition according to claim 10 wherein said detergent is selected from the group consisting of sodium lauryl sulfate and polyoxyethylene 40 stearate.

12. The composition according to claim 1 further comprising water.

13. The composition according to claim 1 further comprising a free fatty acid having between 16 and 18 carbons in length.

14. The composition according to claim 13 wherein said fatty acid is selected from the group consisting of stearate and palmitate.

15. The composition according to claim 1 further comprising a pH stabilizer to buffer the composition and increase the therapeutic longevity thereof.

16. The composition according to claim 15 wherein said stabilizer is glycine.

17. The composition according to claim 1 further comprising optional inert enhancer ingredients which promotes delivery of the thymopentin to the skin.

18. The composition according to claim 17 wherein said ingredients are selected from the group consisting of M pyrol, citrate, maleic acid, EDTA, and carbopol.

19. The composition according to claim 1 having a pH of about 7.

20. A therapeutic composition for use in the treatment of a skin disorder comprising between about 0.1 to about 10% by weight of thymopentin in a pharmaceutically acceptable carrier suitable for topical administration directly onto the surface of the skin, which carrier consists essentially of about 30% of a fatty acid alcohol; about 3 to 4% glycerin; about 2-5% detergent; about 30 to 35% petroleum jelly; about 0 to 2% of a free fatty acid; and the balance of water.

21. The composition according to claim 20 further comprising a pH stabilizer, one or more optional enhancers and one or more preservatives.

22. A therapeutic composition for use in the treatment of a skin disorder comprising between about 0.1 to about 10% by weight of thymopentin in a pharmaceutically acceptable carrier suitable for topical administration directly onto the surface of the skin, which carrier consists essentially of about 2-7% of a fatty acid alcohol; about 1 to 3% glycerin; about 5 to 15% mineral oil; about 5 to 7% detergent; about 0–3% of a free fatty acid; about 50–70% purified water; about 0 to 10% pH stabilizer, and about 0 to 0.3% preservative.

23. A therapeutic composition for use in the treatment of a skin disorder consisting essentially of about 10% thymopentin, about 7% of a combination of cetyl and steryl alcohols; about 1% glycerin; about 15% mineral oil; about 50.7% purified water; about 10% glycine, about 6% detergents and about 0.3% preservative.

24. A method for reducing the irritation of a skin disorder comprising administering directly onto a skin disorder of a mammal in need of such treatment, a topical formulation containing an effective amount of thymopentin or an analog thereof in a pharmaceutically acceptable carrier.

25. The method according to claim 24 wherein said skin disorders are selected from the group consisting of eczema, psoriasis, herpes simplex lesions, poison ivy, atopic dermatitis, chronic dermatitis, contact dermatitis and irritant dermatitis.

26. A method for the preparation of a topical formulation of thymopentin or an analog thereof comprising distributing evenly throughout an emulsion an effective amount of thymopentin micronized to a high micron size of approximately 2 to 5 microns; and providing the composition with a pH of about 7.

* * * * *